United States Patent [19]
Lester

[11] 4,354,933
[45] Oct. 19, 1982

[54] IMPLANTABLE ARTIFICIAL KIDNEY
[76] Inventor: James P. Lester, 3506 Granny White Pike, Nashville, Tenn. 37204
[21] Appl. No.: 236,801
[22] Filed: Feb. 23, 1981
[51] Int. Cl.³ .................. B01D 31/00; A61M 1/03
[52] U.S. Cl. .................. 210/257.2; 128/214 R; 210/262; 210/321.3; 210/512.1; 210/323.2
[58] Field of Search ............ 210/321.3, 321.4, 321.5, 210/487, 927, 257.2, 262, 323.2, 512.1; 128/214 R

[56] References Cited
U.S. PATENT DOCUMENTS 3,505,686  4/1970  Bodell .................. 210/321.4 X
3,893,926  7/1975  Awad ................... 210/321.5
4,071,444  1/1978  Ash et al. ............. 210/321.3 X Primary Examiner—Frank A. Spear, Jr.
Attorney, Agent, or Firm—Harrington A. Lackey

[57] ABSTRACT

An artificial kidney adapted to be implanted in the human body comprising a housing including a diffusion chamber and a dialysate bath chamber. A plurality of microtubules, preferably torqued or spiraled, are arranged substantially vertically in the diffusion chamber. Each microtubule has at least three longitudinal passages therethrough, an arterial passage, a venous passage, and at least one urinary passage, one of the urinary passages extending co-extensively between the arterial and the venous passages, and being separated by walls permeable to waste products from the bloodstream. The arterial and venous blood from the body flow countercurrently through each microtubule, so that the chemical imbalance between the arterial bloodstream and the venous bloodstream causes diffusion across the urinary passage, and the waste products are collected in, and discharged from, the urinary passage. Venous blood from the body is first transported through the dialysate bath chamber for chemical enrichment prior to its flow through the venous passages in the microtubules. The only external function required for operating the kidney is the occasional re-supply of dialysate solution into the dialysate bath.

13 Claims, 8 Drawing Figures

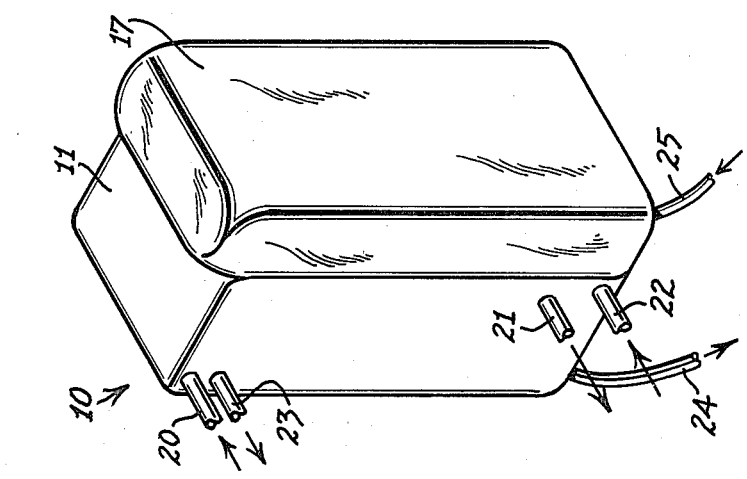
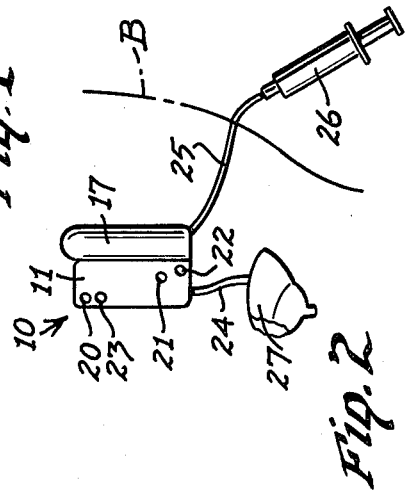
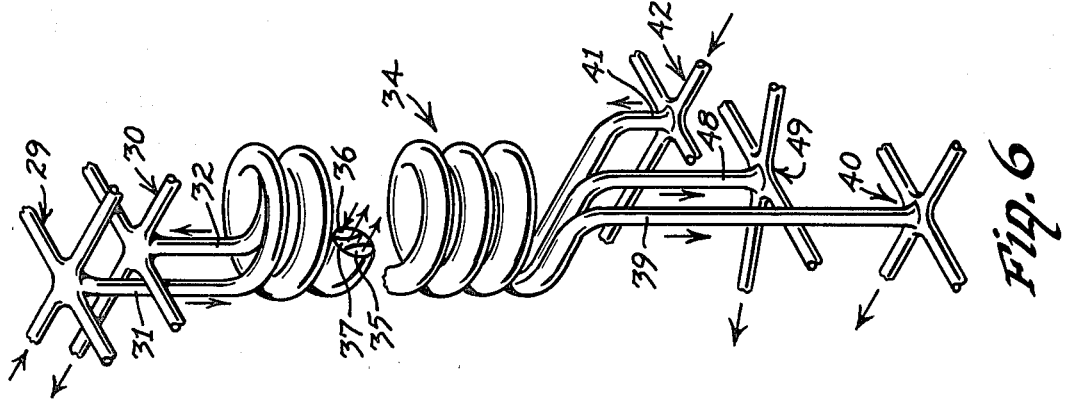
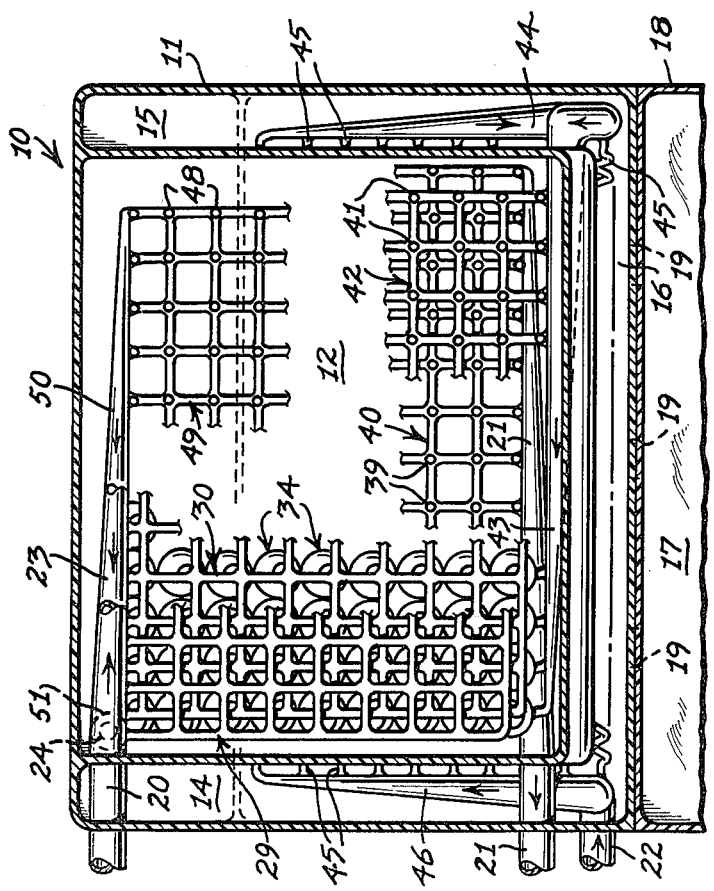
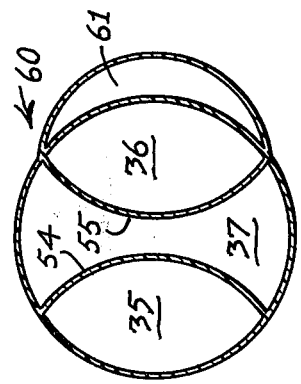
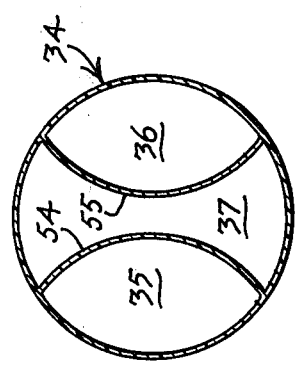

IMPLANTABLE ARTIFICIAL KIDNEY

BACKGROUND OF THE INVENTION

This invention relates to artificial kidneys, and more specifically to an implantable artificial kidney.

Most hemodialysis is conducted with equipment external to the human body, which is connected to an artery and a vein of the patient, in order to circulate the patient's blood through a mechanical hemodialyzer.

Moreover, most hemodialyzers cause the blood from the artery to move through or over a dialysate solution separated by a porous or permeable wall or membrane causing the desirable chemical elements from the dialysate bath to diffuse through the membrane and into the bloodstream to replenish the chemicals needed by the bloodstream. Examples of some of these prior art hemodialyzers are disclosed in the following U.S. patents:

| 3,370,710 | Bluemle, Jr. | Feb. 27, 1968 |
| --- | --- | --- |
| 3,373,876 | Stewart | March 19, 1968 |
| 3,505,686 | Bodell | Apr. 14, 1970 |
| 3,704,223 | Hans-Joachim Dietzsch et al | Nov. 28, 1972 |
| 3,864,259 | Newhart | Feb. 4, 1975 |
| 3,884,808 | Scott | May 20, 1975 |
| 4,176,069 | Metz et al | Nov. 27, 1979 |

Only FIG. 10 of the Bodell U.S. Pat. No. 3,505,686 discloses an artificial implantable kidney, in which the blood flows through an artificial bypass tube in which a plurality of smaller dialysate tubes are immersed, and dialysate solutions continuously provided to the system from an external source.

None of the above patents, or any other prior hemodialyzers known to the applicant, utilize counter-current flow of arterial and venous blood in combination with a co-extensive urinary passage for waste products in the same tubular or microtubular unit to cause a cross-diffusion of chemical elements between the arterial and the venous blood streams.

SUMMARY OF THE INVENTION

It is therefore an object of this invention to provide an artificial kidney which is implantable within the body of the patient, without the necessity of any external mechanism for operating the kidney, except for the periodic supply of the dialysate solution.

The artificial kidney made in accordance with this invention includes a housing having a diffusion chamber and a dialysate bath chamber. Within the diffusion chamber are a plurality of microtubules, each microtubule having an arterial passage, a venous passage, and at least one urinary passage, all being co-extensive longitudinally within each microtubule. Each arterial passage is connected through an inlet arterial manifold and an outlet arterial manifold to corresponding artery sections within the patient's body. Likewise, each venous passage is connected through a corresponding venous inlet manifold and a venous outlet manifold to corresponding vein sections within the patient's body.

However, the venous inlet manifold is in fluid communication with a plurality of venous tubules or microtubules which extend through a portion of the dialysate bath, between the venous inlet manifold and the corresponding natural vein section introducing venous blood into the artificial kidney.

The urinary passage in each microtubule has an outlet manifold which is connected to the urine bladder for deposit of the waste products received in the urinary passages of each of the microtubules.

The connection of the microtubules to the arteries and veins within the body of the patient are such as to cause counter-current flow in each microtubule between the arterial bloodstream and the venous bloodstream.

Moreover, the diffusion chamber is maintained under a pressure slightly in excess of the pressure within each of the microtubules, to cause the cross-diffusion of the unbalanced chemical elements between the arterial and venous passages through the urinary passages. This pressure may be created in the diffusion chamber in its original manufacture and maintained by the complete sealed enclosure of the diffusion chamber.

Alternatively, the pressure may be created by coating or otherwise sealing the exterior wall of each microtubule, so that there can be no external diffusion of any of the fluids or chemical components from the microtubules except internally through the permeable walls separating the respective arterial, venous and urinary passages.

By virtue of the diffusion chamber and the microtubules, which are preferably torqued or arranged in spiral configuration substantially vertically, a smaller dialysate bath chamber and bath liquid is required, because part of the dialysis process is carried out within the diffusion chamber between the counter-current arterial and venous bloodstreams. The utilization of a smaller dialysate bath chamber and an artificial kidney therefore permits smaller kidney units, which are more manageable and easier to implant in the human body.

Of course, where the dialysis needs are greater, multiple kidney units may be implanted.

It is also within the scope of this invention to provide in each microtubule a fourth passage, or second urinary passage, disposed on the opposite side of the venous passage from the first urinary passage in order to collect additional waste products. In forming the spiral configuration of each microtubule, it is preferable to have the second urinary passage disposed radially outward of the venous passage in order for the second urinary passage to collect waste products by virtue of the centrifugal force created by the spiral flow of the bloodstreams within the microtubules.

BRIEF DESCRIPTION OF THE DRAWINGS

FIG. 1 is a top front perspective view of the artificial kidney made in accordance with this invention;

FIG. 2 is a schematic side elevation on a reduced scale of the artificial kidney in its implanted position;

FIG. 5 is a sectional view taken along the line 5—5 of FIG. 3;

FIG. 6 is an enlarged, fragmentary, perspective view of one of the microtubules connected to the various manifolds, shown fragmentarily;

FIG. 7 is a greatly enlarged cross-section of one form of microtubule for the diffusion chamber, having three flow passages; and FIG. 8 is a sectional view similar to FIG. 7 disclosing a modified microtubule having four flow passages.

DESCRIPTION OF THE PREFERRED EMBODIMENTS

Figure 4:
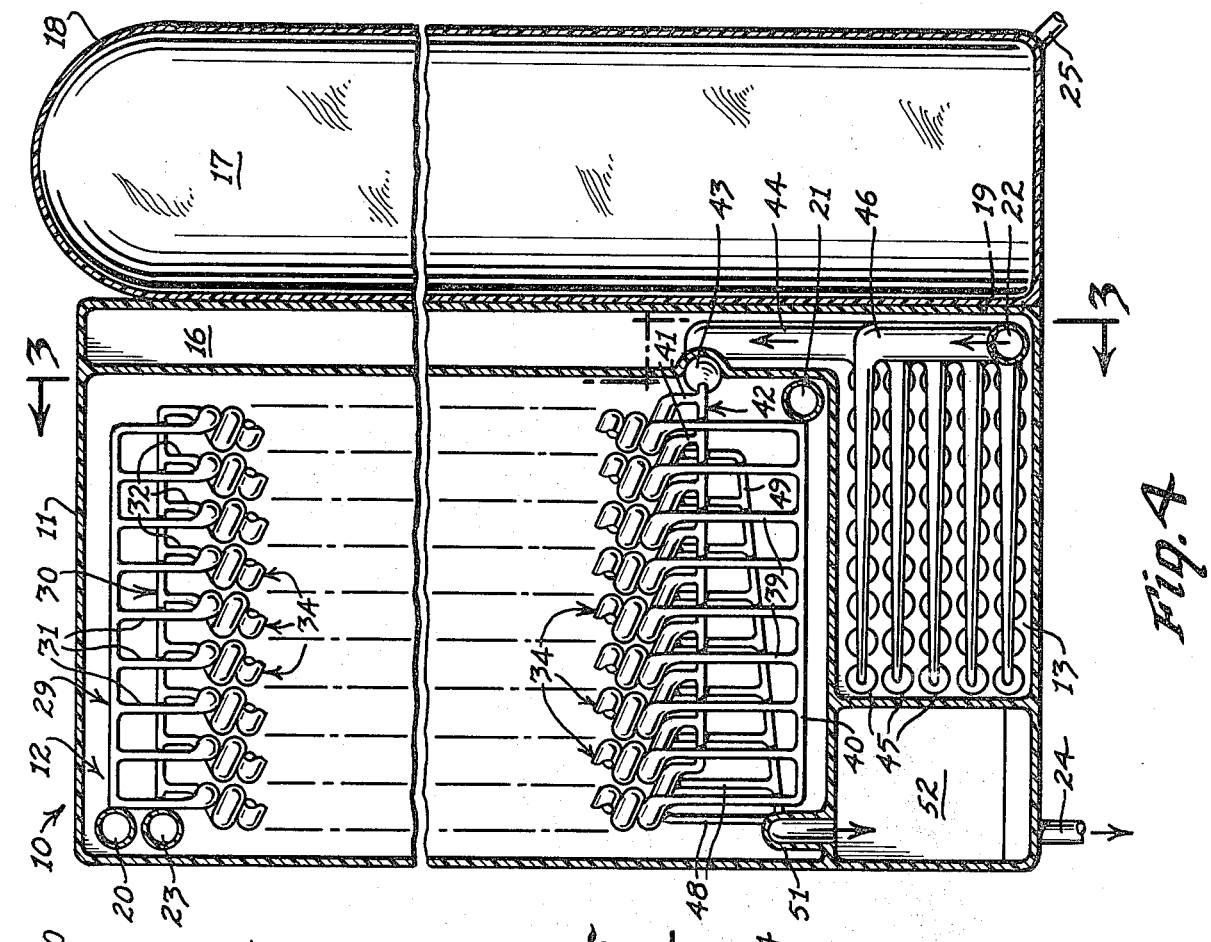
FIG. 4 is a section taken along the line 4—4 of FIG. 3.
Figure 3:
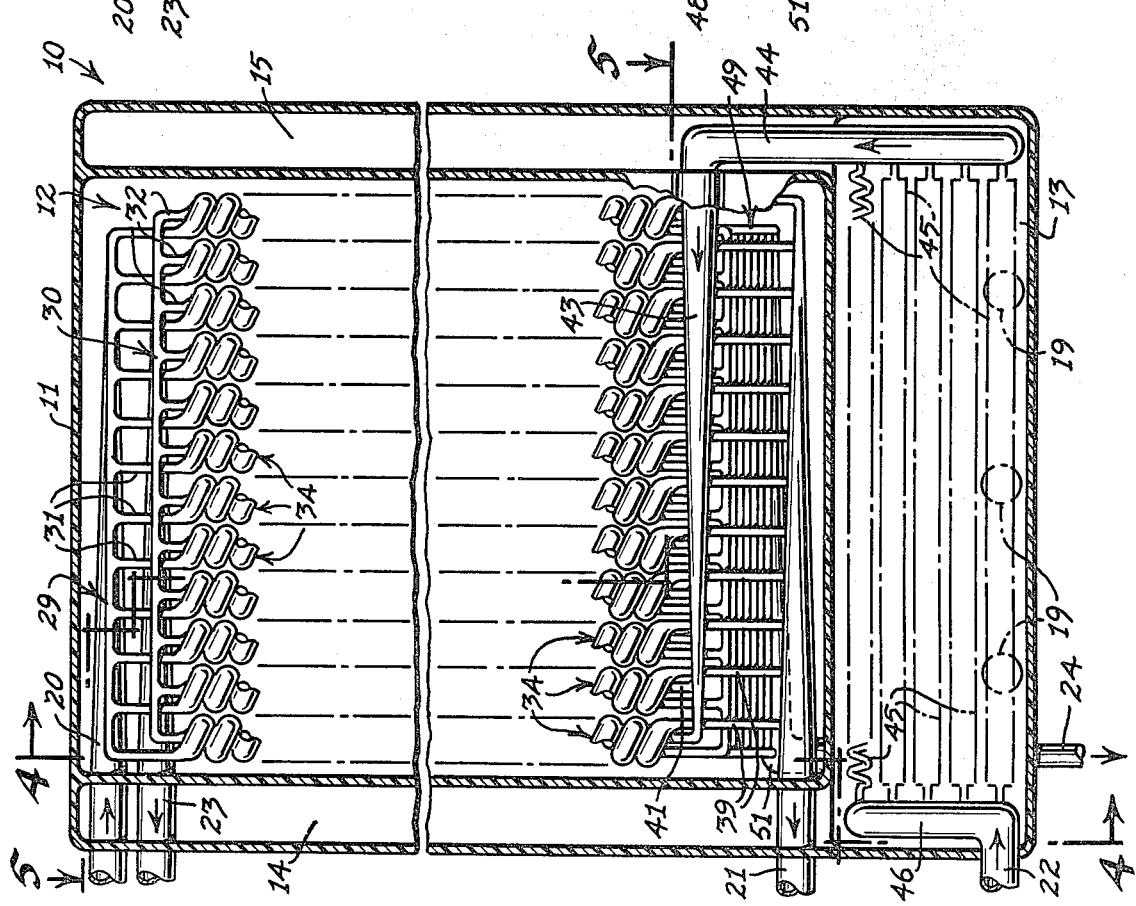
FIG. 3 is an enlarged front sectional elevation of the kidney, taken along the line 3—3 of FIG. 4.

Referring now to the drawings in more detail, FIGS. 1 and 2 disclose an artificial kidney unit 10 made in accordance with this invention adapted to be implanted into the body B of a human being or patient for effecting hemodialysis.

The kidney unit 10 includes a housing 11 broadly divided into a diffusion chamber 12 and a dialysate bath chamber 13. As disclosed in the drawings, the main dialysate bath chamber 13 in the bottom portion of the housing 11 may be supplemented by side bath chamber portions 14 and 15 and front bath chamber portion 16 (FIG. 4), which extend upward to surround the diffusion chamber 12. Additional dialysate bath solution capacity may be provided by an auxiliary bath chamber 17 having a flexible and collapsible wall 18. The auxiliary bath 17 is in fluid communication with the main bath chamber 13 through the port connections 19.

The housing 11 is provided with an upper arterial inlet conduit 20, a lower arterial outlet conduit 21, a lower venous inlet conduit 22, and an upper venous outlet conduit 23. The housing 11 is also provided with a urinary outlet conduit 24. An inlet dialysate conduit 25 connects the auxiliary bath chamber 17 with a source of dialysate solution externally of the body B, such as a syringe 26 (FIG. 2).

The urinary outlet conduit 24 may be connected directly to the human bladder 27 (FIG. 2).

The portion of the arterial inlet conduit 20 extends across the upper portion of the interior of the housing 11 and within the diffusion chamber 12, gradually diminishing in cross-section to maintain a substantially uniform fluid pressure of the incoming arterial blood throughout the length of the inlet portion 20 within the diffusion chamber 12. Communicating with the tapered portion of the arterial inlet conduit 20 at uniform spaced intervals along its length are a plurality of transversely spaced longitudinal tubes forming a grid network of tubes, including lateral tubes, to form a gridlike inlet manifold 29 for the arterial blood.

In a similar manner, the venous outlet conduit 23 tapers across the upper portion of the diffusion chamber 12 beneath the arterial inlet grid manifold 29 and is connected in the same manner to substantially an identical grid network of tubes forming a venous outlet manifold 30 for discharging venous blood from the kidney unit 10.

Depending from each intersection of the longitudinal and lateral tubules in the arterial inlet manifold 29 is a depending branch inlet tubule 31. In the same manner, depending from each of the intersections of the gridlike outlet venous manifold 30 is a depending branch outlet tubule 32.

Suspended in substantially vertical parallel relationship within the diffusion chamber 12 are a plurality of elongated tri-chambered microtubules 34. Each microtubule 34 is preferably torqued or arranged in a spiral configuration, as disclosed in FIG. 6, in order to lengthen the flow paths through each microtubule and also to provide a certain amount of centrifugal force to facilitate diffusion within each microtubule 34.

Each microtubule 34 includes an elongated, co-extensive arterial passage 35, an elongated co-extensive venous passage 36, and an elongated co-extensive urinary passage 37 between the arterial passage 35 and the venous passage 36. The upper end portion of each arterial passage 35 is connected to, and in free fluid communication with, a corresponding depending arterial branch inlet tubule 31, and each of the venous passages 36 is connected at its upper end in fluid communication with a corresponding depending branch outlet tubule 32. The upper end portion of each urinary passage 37 is closed.

The lower end portion of each arterial passage 35 is in fluid communication with a branch arterial outlet tubule 39, which is connected to the intersection of the gridlike network of tubules in an arterial outlet manifold 40 of substantially identical construction to the arterial inlet manifold 29. The arterial outlet manifold 40 is connected to the arterial outlet conduit 21.

The bottom portion of each of the venous passages 36 is in fluid communication with a depending branch inlet tubule 41 connected to a corresponding intersection of the tubular grid network of a venous manifold 42, which in turn is connected to an intermediate venous conduit 43.

The intermediate conduit 43 is in turn connected to an outlet header conduit 44 disposed in the bath chamber 15 and extending down into the main bath chamber 13 where it is connected to a plurality of spiraled venous tubules 45 extending horizontally through the bath chamber 13 to an inlet header conduit 46. The inlet header conduit 46 is in turn connected to the venous inlet conduit 22.

The lower end of each urinary passage 37 is in fluid communication with each depending branch outlet 48, which is likewise connected to the intersection of a grid network urinary outlet manifold 49. The urinary outlet manifold 49 discharges the waste products through a urinary outlet tube 50 and a fluid nipple 51 into a urinary chamber 52 which in turn is in fluid communication with the urinary outlet conduit 24.

The housing 11 may be made of any material which is hypoallergenic, non-hemolytic and non-degradable, such as polymethlymethacrylate or cellulose acetate.

The tri-chambered tubules 34, and particularly the inner walls 54 and 55 separating the three chambers 35, 37 and 38, as well as the venous tubules 45, must be made of a permeable material, such as cellulose acetate, in order to permit the diffusion of the chemical components of the blood as well as the waste products through these permeable membranes.

Where the exterior wall of each microtubule 34 is not coated or sealed, then a slightly excessive pressure is formed and maintained within the diffusion chamber 12 such that this pressure will exceed the internal pressures within the microtubules 34, causing internal diffusion or tranfusion between the various passageways 35, 37 and 36.

The bath chambers 13, 14, 15, 16 and 17 are filled with a conventional dialysate solution. A typical dialysate bath solution would consist of:

Solium Chloride
Sodium Acetate Trihydrate
Potassium Chloride
Calcium Chloride
Magnesium Chloride Hexahydrate
Glucose
Urease
Activated charcoal
Water The microtubules 34 are also coiled in spiral configuration in order to greatly increase the diffusion surface areas, and particularly the surface areas or lengths of the corresponding inner permeable walls 54 and 55, within a diffusion chamber 12 of a given size.

It will be noted that the manner in which the microtubules 34 are connected to the respective inlet and outlet conduits permits arterial blood to pass into the top of the diffusion chamber 12 and flow downward through each of the microtubules 34 by gravity, as well as by the pressure exerted by the natural pump, the heart. Simultaneously, the venous blood flows upward through the same microtubules 34 counter-current to the arterial flow, thereby increasing the diffusion capability of each microtubule 34.

The number of microtubules that are positioned within a kidney unit 10 are directly proportional to the amount of filtration the kidney unit 10 can maintain.

In the preferred form of the invention the venous passage 36 is preferably approximately twice the cross-sectional area as the arterial passage 35, since the venous bloodstream is additionally treated by the dialysis bath in the chamber 13, whereas the arterial bloodstream does not pass through such bath.

As the arterial and venous streams of blood flow counter-current through their respective arterial and venous passages 35 and 36 in each of the microtubules 34, a chemical ionic exchange occurs between the two bloodstreams across the urinary passage 37, and waste products from both bloodstreams collect in the central urinary passage 37 to flow downwardly for ultimate discharge from the kidney unit 10.

Before the kidney unit 10 is implanted in the body 11 of the patient, it is preferable to provide an initial priming component within the urinary passage 37 in order to initiate the diffusion between the counter-current bloodstream in each microtubule 34.

The function of the microtubules 34 within the diffusion chamber 12 approximates diffusive action within a human kidney, with the exception that this kidney unit utilizes the arterial and venous counter-current flow to establish the chemical gradient, as opposed to the water-based fluid found in the nephronic tubules in the normal human kidney. Otherwise, the principle of kidney action is substantially the same by virtue of the diffusion action of the microtubules 34 plus the replenishment of the venous bloodstream, before it enters the microtubule diffusion system, with the dialysate solution in the bath chamber 13. Dialysis can be maintained without the use of a pump or recirculating dialysate solution, provided the dialysate bath is replenished periodically.

The arterial and venous inlet and outlet conduits 20, 21, 22, and 23 are connected to corresponding arteries and veins by conventional surgical procedures, such as anastomosis.

FIG. 8 discloses the cross-section of a modified microtubule 60 having the same arterial passage 35, venous passage 36 and innermediary urinary passage 37, but including an additional or second urinary passage 61 formed on the opposite side of the venous passage 36 from the first urinary passage 37. When the microtubules 60 are coiled in spiral configuration, preferably the second urinary passage 61 lies radially outward of the other passages so that centrifugal force will not only assist the diffusion of chemical substances from the arterial passage 35 into the urinary passage 37, but will also assist in diffusing waste products from the venous passage 36 into the second urinary passage 68. The bottom portion of the urinary passage 61 is connected in the same manner, not shown, to the urinary outlet manifold network system 49 as is the first urinary passage 37.

Moreover, a second urinary chamber 61 provides an additional waste receptacle for waste products, such as sodium ions, carbonate ions, and carbon dioxide, if such ions or waste products become excessive in the first urinary passage 37.

It is preferably that the permeable walls or membranes 54 and 55 are impermeable to the blood proteins, but are permeable to nitrogenous body waste products, such as urea, acid and creatine.

The walls of the venous tubules 45 should also be made of the same permeable material as the microtubule walls 54 and 55 so that waste products can be partially removed from the venous blood in the tubules 45 and chemical elements from the dialysis bath in the bath chamber 13 can diffuse into the tubules 45 to enrich the venous blood.

The urinary discharge chamber 52 may be provided with a weight sensitive valve in the port connecting with the artificial urethra or urinary outlet conduit 24 so that the waste products will be eliminated from the discharge chamber 52 only at periodic intervals, if desired.

What is claimed is:

1. An artificial kidney comprising:
   (a) a least one elongated microtubule having first and second end portions,
   (b) said microtubule having longitudinally co-extensive arterial and venous passages and a urinary passage longitudinally co-extensive between said arterial and venous passages,
   (c) said urinary passage having first and second opposed walls separating respectively said arterial passage and said venous passage from said urinary passage, said opposed walls being permeable to the flow of waste products in the bloodstreams respectively from said arterial and venous passages into said urinary passage,
   (d) means for connecting the first and second end portions of said microtubule to an artery and a vein in a human body to cause arterial blood to flow in one direction through said arterial passage and venous blood to flow in the opposite direction through said venous passage, and
   (e) means for discharging the contents of said urinary passage.

2. The invention according to claim 1 further comprising a dialysate bath chamber, and venous conduit means for conveying venous blood from a vein in the human body through, and in diffusive communication with, said dialysate bath chamber to the venous passage in said microtubule, and means for introducing a dialysate solution into said dialysate bath chamber.

3. The invention according to claim 2 further comprising a housing including a diffusion chamber and said dialysate bath chamber, said microtubule being contained within said diffusion chamber.

4. The invention according to claim 3 further comprising an arterial inlet in said housing in fluid communication with the arterial passage in the first end portion of said microtubule, an arterial outlet in said housing in fluid communication with the arterial passage in the second end portion of said microtubule, a venous inlet in said housing in fluid communication with said venous conduit means, said venous conduit means being in fluid communication with the venous passage in said second end portion of said microtubule, a venous outlet in said housing in fluid communication with the venous passage in the first end portion of said microtubule, and a urinary outlet in said housing in fluid communication with the urinary passage in the second end portion of said microtubule.

5. The invention according to claim 4 in which the first end portions of said microtubules are all disposed above said second end portions in said diffusion chamber.

6. The invention according to claim 5 in which each of said microtubules is torqued in substantially uniform spiral configurations, each spiral microtubule having a generally vertical axis.

7. The invention according to claim 6 further comprising an arterial inlet manifold in the upper portion of said diffusion chamber, having an inlet portion in fluid communication with said arterial inlet and having an arterial branch outlet in fluid communication with the arterial passage in the first end portion of each of said microtubules, a venous outlet manifold in the upper portion of said diffusion chamber having an outlet portion in fluid communication with said venous outlet and having a venous branch inlet in fluid communication with the venous passage in the first end portion of each of said microtubules, and an arterial outlet manifold in the lower portion of said diffusion chamber having an outlet portion in fluid communication with said arterial outlet and having a branch inlet in fluid communication with the arterial passage in the second end portion of each of said microtubules.

8. The invention according to claim 6 in which said venous conduit means comprises a plurality of permeable venous tubules extending through said dialysate bath chamber and having inlet portions in fluid communication with said venous inlet and outlet portions, a venous inlet manifold having an inlet portion in fluid communication with the outlet portions of said venous tubules and having a plurality of venous branch outlets, each branch outlet being in fluid communication with the venous passage of the second end portion of each of said microtubules.

9. The invention according to claim 8 in which said dialysate bath chamber has an inlet conduit adapted to be connected in fluid communication with a source of dialysate externally of the body of the person in which said housing is implanted.

10. The invention according to claim 6 further comprising a urinary outlet manifold having a plurality of branch inlets, each in fluid communication with the urinary passage in the second end portion of each of said microtubules, and an outlet passage in fluid communication with said urinary outlet.

11. The invention according to claim 6 further comprising a flexible dialysate bath reservoir fixed to said housing and in fluid communication with said dialysate bath chamber.

12. The invention according to claim 1 further comprising a second urinary passage co-extensive in each of said microtubles on the opposite side of said venous passage from said first urinary passage, a third wall separating said venous passage from said second urinary passage, said third wall being permeable to the flow of waste products in the bloodstream carried in said venous passage, said second urinary passage being in fluid communication with said means for discharging the contents of said urinary passage.

13. The invention according to claim 1 further comprising means for maintaining an external pressure on each of said microtubules in excess of the internal pressure within said microtubule.

* * * * *